United States Patent
Brierley

(10) Patent No.: US 10,365,262 B2
(45) Date of Patent: Jul. 30, 2019

(54) METHOD OF MONITORING A PARAMETER OF A HYDROCARBON WELL, PIPELINE OR FORMATION

(71) Applicant: JOHNSON MATTHEY PUBLIC LIMITED COMPANY, London (GB)

(72) Inventor: Aidan Brierley, Cleveland (GB)

(73) Assignee: Johnson Matthey Public Limited Company, London, England (GB)

( * ) Notice: Subject to any disclaimer, the term of this patent is extended or adjusted under 35 U.S.C. 154(b) by 0 days.

(21) Appl. No.: 15/765,735

(22) PCT Filed: Oct. 5, 2016

(86) PCT No.: PCT/GB2016/053102
§ 371 (c)(1),
(2) Date: Apr. 4, 2018

(87) PCT Pub. No.: WO2017/060702
PCT Pub. Date: Apr. 13, 2017

(65) Prior Publication Data
US 2018/0284096 A1    Oct. 4, 2018

(30) Foreign Application Priority Data
Oct. 7, 2015   (GB) .................................. 1517744.7

(51) Int. Cl.
| G01N 33/24 | (2006.01) |
| E21B 47/10 | (2012.01) |
| C09K 8/58 | (2006.01) |
| C09K 8/035 | (2006.01) |
| G01N 31/22 | (2006.01) |
| E21B 49/00 | (2006.01) |
| E21B 49/08 | (2006.01) |

(52) U.S. Cl.
CPC ............. *G01N 33/24* (2013.01); *C09K 8/035* (2013.01); *C09K 8/58* (2013.01); *E21B 47/1015* (2013.01); *E21B 49/00* (2013.01); *E21B 49/08* (2013.01); *G01N 31/22* (2013.01)

(58) Field of Classification Search
CPC ........ G01N 33/24; G01N 31/22; C09K 8/035; C09K 8/58; E21B 47/1015; E21B 49/00; E21B 49/08
See application file for complete search history.

(56) References Cited

U.S. PATENT DOCUMENTS

| 8,640,773 B2 | 2/2014 | Hewitt et al. | |
| 2011/0260051 A1* | 10/2011 | Preudhomme | E21B 43/16 250/282 |
| 2013/0126158 A1 | 1/2013 | Hinamoto et al. | |
| 2015/0323515 A1* | 11/2015 | Rule | G01N 33/241 166/250.12 |
| 2016/0003040 A1* | 1/2016 | Jessheim | B09C 1/00 507/205 |
| 2017/0198200 A1* | 7/2017 | Sayfritz | E21B 49/08 |
| 2018/0030331 A1* | 2/2018 | Stray | C09K 8/58 |

FOREIGN PATENT DOCUMENTS

| EP | 1277051 A1 | 1/2003 |
| EP | 2563874 A1 | 3/2013 |
| WO | WO 2011/135481 A1 | 3/2011 |
| WO | WO 01/81914 A1 | 11/2011 |
| WO | WO 2014/096459 A1 | 6/2014 |
| WO | WO 2015/069596 A1 | 5/2015 |
| WO | WO 2016/124778 A1 | 8/2016 |

OTHER PUBLICATIONS

PCT/GB2016/053102 International Search Report and Written Opinion dated Jan. 18, 2017.
GB1517744.7 Search Report Under Section 17(5) dated May 16, 2016.
GB1616922.9 Combined Search and Examination Report Under Sections 17 and 18(3) dated Apr. 28, 2017.

* cited by examiner

*Primary Examiner* — Zakiya W Bates
*Assistant Examiner* — Crystal J Miller
(74) *Attorney, Agent, or Firm* — BakerHostetler

(57) ABSTRACT

A method of monitoring a parameter of a hydrocarbon well, pipeline or formation is provided. The method comprises introducing a tracer into the hydrocarbon well, pipeline or formation; producing a fluid from the hydrocarbon well, pipeline or formation; and analyzing the fluid to determine if the tracer is present in the fluid. The tracer comprises a halogenated alkoxylated-benzoic acid, an alkoxylated benzene sulfonic acid, a salt of a halogenated alkoxylated-benzoic acid or a salt of an alkoxylated benzene sulfonic acid.

24 Claims, 1 Drawing Sheet

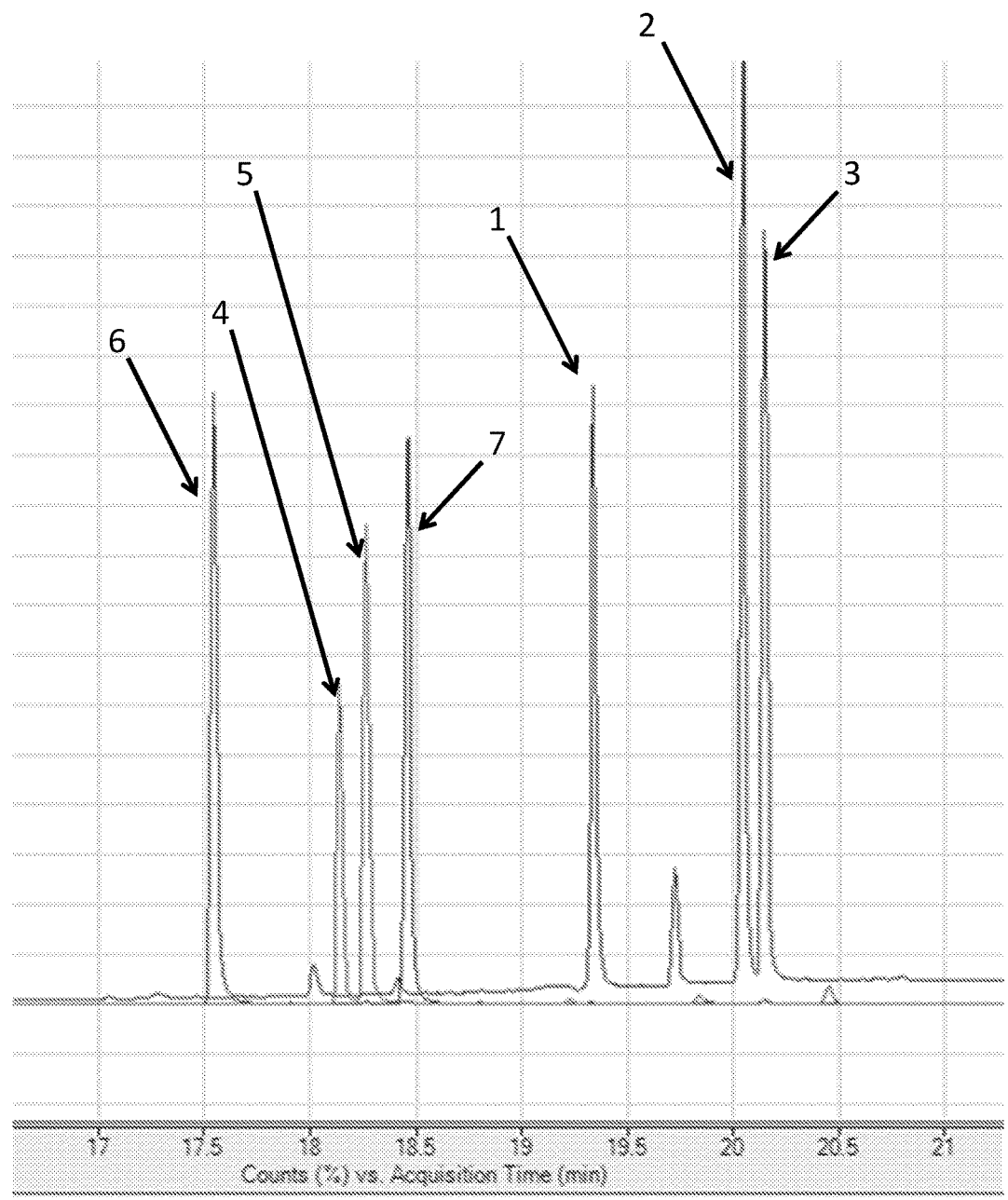

METHOD OF MONITORING A PARAMETER OF A HYDROCARBON WELL, PIPELINE OR FORMATION

CROSS-REFERENCE TO RELATED APPLICATIONS

This application is the National Stage of International Patent Application No. PCT/GB2016/053102, filed Oct. 5, 2016, which claims priority from Great Britain Patent Application No. 1517744.7, filed Oct. 7, 2015, the disclosures of each of which are incorporated herein by reference in their entireties for any and all purposes.

FIELD OF THE INVENTION

The present invention relates to use of tracers in monitoring of hydrocarbon wells, pipelines or formations and methods of monitoring hydrocarbon wells, pipelines or formations. More specifically, but not exclusively, the invention relates to tracers for monitoring the relative production of water from different zones of hydrocarbon wells and methods of monitoring the relative production of water from different zones of hydrocarbon wells.

BACKGROUND

The use of tracers to monitor aspects of the performance of hydrocarbon wells is an established technique. The tracers may be water tracers, in that they are predominantly soluble in water, oil tracers, in that they are soluble in the hydrocarbons in the formation, or partitioning tracers, in that they move between the water and hydrocarbon or back. Some tracing methods will more than one type of tracer and use the difference in behaviour to deduce properties of the hydrocarbon formation. For example, partitioning and water tracers may be injected into a production well along with injected water and then monitored as they are subsequently produced from the well. The time difference between the production of the water tracers, which are produced with the returning injected water, and the partitioning tracers, whose production is delayed by their interaction with the hydrocarbons in the formation, can be used to deduce parameters relating to the local remaining hydrocarbon content of the formation. Alternatively, applications may use only water tracers. For example, water tracers may be introduced in an injection well and their presence monitored at adjacent production wells in order to obtain information about the flux of water from the injection well to the production well.

In addition to injected techniques, it is also known to introduce tracers into a well by including them in articles placed into the well. For example, the tracers may be mixed with a polymer and cast into an article that is inserted into the well when the well is constructed. The tracer is then eluted from the polymer over time as fluid flows past the article. By detecting the rate of tracer production over time, information can be deduced about production of water or oil in the reservoir.

Examples of tracer techniques are described in EP1277051 and U.S. Pat. No. 8,640,773.

Many tracing techniques measure a property of a region of a well or formation relative to the properties of surrounding regions of the well or formation. In order to do that, different tracers are introduced into the different regions, whether by injection, placement during well construction, or another method. The production of each of the different tracers can be monitored in samples produced from the well to obtain information about where the produced fluids have come from. In addition, tracing techniques may be used sequentially on wells that have previously been traced. As an example, an inter-well tracer study may be used to monitor injected water flux from an injection well to a production well and a later study may then inject tracers into the same injection well or a different well to monitor the levels of hydrocarbon remaining in the well. If the same tracer is used for two different regions, or in two different studies, the analysis of the produced sample may be contaminated by tracer from the wrong region or the previous study. In a typical ("conventional") well, there may be demand for studies involving 10-20 different tracers, but for some applications, for example hydraulic fracturing applications, it may be desirable to monitor as many as 40 different zones per lateral bore, with several laterals in a well. There is therefore a need for new tracers and in particular a need for new families of tracers.

Fluorinated benzoic acid salts are often used as water tracers in hydrocarbon well monitoring. A number of possible tracer variants exist in the fluorinated benzoic acid family since the benzoic acid can be mono-, di-, tri-, tetra- or penta-fluorinated and the fluorination can, except for the penta-fluorinated case, be at various locations on the aromatic ring. Nevertheless, there are a finite number of variants of fluorinated benzoic acids.

In order to be useful as a tracer, a compound should be thermally stable in that it should be stable at the temperatures typically encountered in wells, which may be 60 to 90° C. Desirably, a tracer is stable in temperatures up to maybe 160 or 180° C. so as to permit use in high temperature wells. For a water tracer, the compound should be highly selective toward water over oil. The compound should also be detectable in very small quantities, preferably at levels of 10 ppb or lower and most preferably in the parts per trillion (ppt) range (that is, at levels less than 1 ppb). The levels are determined on a mass/mass basis. The compound should also be environmentally acceptable, for inserting into the ground, but also not a compound that is naturally present in the ground in such quantities as to contaminate the results of the tracer study.

Typical detection methods include gas chromatography mass spectrometry (GC-MS), gas chromatography mass spectrometry mass spectrometry (GC-MS-MS), liquid chromatography mass spectroscopy (LC-MS), liquid chromatography mass spectroscopy mass spectroscopy (LC-MS-MS) and high pressure liquid chromatography (HPLC), which can typically detect very low concentrations of the tracers in the produced fluids. It is desirable that tracers should be detectable in low quantities and also that they can be reliably distinguished from other tracers.

Further examples of tracers are disclosed in EP2563874.

Preferred embodiments of the present invention seek to overcome one or more of the above disadvantages of the prior art. In particular, preferred embodiments of the present invention seek to provide new tracer compounds for use in hydrocarbon well monitoring.

SUMMARY OF INVENTION

According to a first aspect of the invention, there is provided use of a tracer in monitoring a parameter of a hydrocarbon well, pipeline or formation, the tracer comprising a halogenated alkoxylated-benzoic acid, an alkoxylated benzene sulfonic acid, a salt of a halogenated alkoxylated-benzoic acid or a salt of an alkoxylated benzene sulfonic acid. Preferably the tracer comprises a salt of a halogenated alkoxylated-benzoic acid or a salt an alkoxylated benzene sulfonic acid.

Thus the tracer of the invention comprises an alkoxylated acid or a salt thereof. The acid is either a benzoic acid or a benzene sulfonic acid. If the tracer is a benzoic acid, the tracer is halogenated.

Preferably the tracer is a water tracer. Thus the use may involve monitoring the flow of water through or from a well or formation. For example the use may determine the source of produced water by introducing the tracer into a defined part of the well or formation and monitoring for the presence of the tracer in produced water. As another example, the use may involve a partitioning study to determine residual oil saturation where the tracer is used as the conservative, water soluble tracer.

In a preferred aspect of the invention the tracer comprises a compound, or a salt thereof, of formula 1:

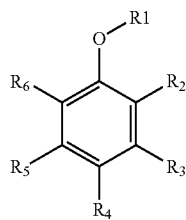

Formula 1 wherein $R_1$ is selected from the group consisting of $C_nF_xCl_yH_{(2n+1-x-y)}$ where n=1, 2 or 3, and x and y are integers such that $0 \leq x+y \leq 2n+1$, wherein at least one of $R_2$, $R_3$, $R_4$, $R_5$ and $R_6$ is carboxylic acid (COOH) or sulfonic acid ($SO_3H$), wherein the remainder of $R_2$, $R_3$, $R_4$, $R_5$ and $R_6$ are selected from the group consisting of F, Cl, Br, H, $B(OH)_2$, $C_mF_jCl_kBr_lH_{(2m+1-j-k-l)}$, where m=1, 2 or 3, each of j, and l are integers such that $0 \leq j+k+l \leq 2m+1$, and O—$C_pF_rCl_sBr_tH_{(2p+1-r-s-t)}$, where p=1, 2 or 3, and r, s and t are integers such that $0 \leq r+s+t \leq 2p+1$, and wherein either at least one of $R_2$, $R_3$, $R_4$, $R_5$ and $R_6$ is sulfonic acid, or at least one of $R_1$, $R_2$, $R_3$, $R_4$, $R_5$ and $R_6$ is halogenated, or both.

Thus an aspect of the invention provides use of a tracer in monitoring a parameter of a hydrocarbon well, pipeline or formation, the tracer comprising a compound, or a salt thereof, of formula 1:

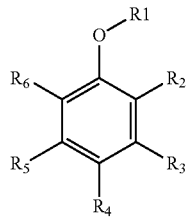

Formula 1 wherein $R_1$ is selected from the group consisting of $C_nF_xCl_yH_{(2n+1-x-y)}$ where n=1, 2 or 3, and x and y are integers such that $0 \leq x+y \leq 2n+1$, wherein at least one of $R_2$, $R_3$, $R_4$, $R_5$ and $R_6$ is carboxylic acid (COOH) or sulfonic acid ($SO_3H$), wherein the remainder of $R_2$, $R_3$, $R_4$, $R_5$ and $R_6$ are selected from the group consisting of F, Cl, Br, H, $B(OH)_2$, $C_mF_jCl_kBr_lH_{(2m+1-r-s-t)}$, where m=1, 2 or 3, each of j, k and l are integers such that $0 \leq j+k+l \leq 2m+1$, and O—$C_pF_rCl_sBr_tH_{(2p+1-r-s-t)}$, where p=1, 2 or 3, and r, s and t are integers such that $0 \leq r+s+t \leq 2p+1$, and wherein either at least one of $R_2$, $R_3$, $R_4$, $R_5$ and $R_6$ is sulfonic acid, or at least one of $R_1$, $R_2$, $R_3$, $R_4$, $R_5$ and $R_6$ is halogenated, or both.

Preferably $R_1$ is selected from the group consisting of $C_nX_yH_{(2n++1-y)}$ where n=1, 2 or 3, $0 \leq y \leq 2n+1$ and X is one of F or Cl. Preferably, $R_1$ is selected from the group consisting of $C_nX_yH_{(2n+1-y)}$ where n=1, 2 or 3, $1 \leq y \leq 2n+1$ and X is one of F or Cl. It may be that, $R_1$ is selected from the group consisting of $CH_3$, $C_2H_5$, $C_3H_7$, $CFH_2$, $CF_2H$, $CF_3$, $CClH_2$, $CCl_2H$ and $CCl_3$. More preferably, $R_1$ is selected from the group consisting of $CH_3$, $CFH_2$, $CF_2H$, and $CF_3$.

Preferably the remainder of $R_2$, $R_3$, $R_4$, $R_5$ and $R_6$ are selected from the group consisting of F, Cl, Br, H, $C_mX_jH_{(2m+1-j)}$ where m=1, 2 or 3, $0 \leq j \leq 2m+1$ and X is one of F, Cl or Br and preferably one of F or Cl, and O—$C_pX_rH_{(2p+1-r)}$, where p=1, 2 or 3, $0 \leq r \leq 2p+1$ and X is one of F, Cl or Br and preferably one of F or Cl. More preferably the remainder of $R_2$, $R_3$, $R_4$, $R_5$ and $R_6$ are selected from the group consisting of F, Cl, Br, H, $CH_3$, $C_2H_5$, $C_3H_7$, $CFH_2$, $CF_2H$, $CF_3$, O—$CH_3$, O—$C_2H_5$, O—$C_3H_7$, O—$CFH_2$, O—$CF_2H$, O—$CF_3$, O—$CClH_2$, O—$CCl_2H$ and O—$CCl_3$. More preferably the remainder of $R_2$, $R_3$, $R_4$, $R_5$ and $R_6$ are selected from the group consisting of F, Cl, Br, H, $CH_3$, $C_2H_5$, $C_3H_7$, $CFH_2$, $CF_2H$, and $CF_3$.

Preferably at least one of $R_1$, $R_2$, $R_3$, $R_4$, $R_5$ and $R_6$ is halogenated. It will be appreciated that when at least one of $R_1$, $R_2$, $R_3$, $R_4$, $R_5$ and $R_6$ is said to be halogenated it means that at least one of $R_1$, $R_2$, $R_3$, $R_4$, $R_5$ and $R_6$ contains at least one halogen atom. For example, at least one of $R_1$, $R_2$, $R_3$, $R_4$, $R_5$ and $R_6$ may be a halogen, such as F, Br or Cl, or at least one of $R_1$, $R_2$, $R_3$, $R_4$, $R_5$ and $R_6$ may be a halogenated group such as $CH_2F$ or $CF_3$. Preferably at least one of $R_1$, $R_2$, $R_3$, $R_4$, $R_5$ and $R_6$ is fluorinated, chlorinated or brominated, more preferably at least one of $R_1$, $R_2$, $R_3$, $R_4$, $R_5$ and $R_6$ is fluorinated or chlorinated and most preferably at least one of $R_1$, $R_2$, $R_3$, $R_4$, $R_5$ and $R_6$ is fluorinated. Halogenation advantageously alters the mass ion detected in a GC-MS analysis and therefore allows the compounds of the invention to be distinguished from naturally occurring compounds in hydrocarbon formations and wells.

While one or more of $R_1$, $R_2$, $R_3$, $R_4$, $R_5$ and $R_6$ may be halogenated when a sulfonic acid group is present, if the tracer comprises a sulfonic acid group, the sulfonic acid group may itself distinguish the compound from naturally occurring compounds in hydrocarbon formations and wells. Thus in some aspects of the invention at least one of $R_2$, $R_3$, $R_4$, $R_5$ and $R_6$ is sulfonic acid and no halogen is present in the tracer. In such aspects of the invention, $R_1$ is preferably selected from the group consisting of $C_nH_{(2n+1)}$ where n=1, 2 or 3. More preferably, $R_1$ is $CH_3$. The remainder of $R_2$, $R_3$, $R_4$, $R_5$ and $R_6$ are selected from the group consisting of H, $C_mH_{(2m+1)}$ where m=1, 2 or 3 and O—$C_pH_{(2p+1)}$, where p=1, 2 or 3. More preferably the remainder of $R_2$, $R_3$, $R_4$, $R_5$ and $R_6$ are selected from the group consisting of H, $CH_3$, $C_2H_5$ and $C_3H_7$.

In some aspects of the invention none of $R_2$, $R_3$, $R_4$, $R_5$ and $R_6$ is sulfonic acid (that is, the acid groups are all carboxylic acid). In that case, at least one of $R_1$, $R_2$, $R_3$, $R_4$, $R_5$ and $R_6$ is halogenated, preferably fluorinated or chlorinated and most preferably fluorinated. Such halogenated alkoxylated benzoic acids may advantageously be easier to handle and provide tracers (from the acid or its salt) having good detectability.

In some aspects of the invention none of $R_2$, $R_3$, $R_4$, $R_5$ and $R_6$ is carboxylic acid (that is, the acid groups are all sulfonic acid). The high solubility of sulfonic acid groups in water may be particularly advantageous for water tracers based on the acids or their salts. The detectability of tracers comprising alkoxylated benzene sulfonic acids or their salts even without halogenation may also be advantageous.

Tracers according to the invention are not naturally found in hydrocarbon wells and formations and have not been previously used as tracers in such wells and formations. Tracers according to the invention may therefore be used as tracers in such wells and formations without the results of the tracing being affected by contamination. Moreover, tracers of the invention may have sufficient thermal stability to survive the conditions in a hydrocarbon well. Such tracers may also be detectable, for example using GC-MS, in very low concentrations, for example concentrations of 10 ppb or less, preferably concentrations of 1 ppb or less, more preferably concentrations of 100 ppt or less, yet more preferably concentrations of 10 ppt or less and still more preferably concentrations of 1 ppt or less. The tracers may show a high selectivity towards water instead of oil. Thus the tracer may be a water tracer. The tracer may have a log P value of less than −1. The log P value is a well-known value for characterising the preference of a compound for water or oil. The value is the log of the ratio of the equilibrium concentration of the compound in oil (octanol) to the equilibrium concentration of the compound in water. Thus the concentration of the compound in water is preferably at least 10 times, and more preferably at least 100 times, that of the compound in oil. It may be that the salt of the compound (or the anion of the salt) is more soluble in water than the acid. For that reason, it is preferable to use the salt as the tracer.

Tracers of the invention may be particularly advantageous in that the tracers comprise an alkoxyl substituent. The presence of the alkoxyl results in a clear distinction between the tracers of the invention and prior art tracers, such as fluorobenzoic acid tracers, when analysed using GC-MS. Moreover, the alkoxyl does not significantly adversely affect the thermal stability or selectivity to water over oil. Thus the provision of an alkoxyl results in a new family of tracer compounds that are distinguishable from each other and from previously used tracer compounds. That may be advantageous in all hydrocarbon well, pipeline or formation tracing applications, but may be particularly advantageous in the tracing of fracking wells, where large quantities of individually distinguishable tracers may be required for even a single tracing study. The tracers of the invention advantageously have detectability equivalent to previously used water tracers.

The parameter monitored may be a parameter related to a property, such as flow or composition, of the well, pipeline or formation and may be an absolute parameter or a relative parameter. A relative parameter may describe a property of one part of the well, pipeline or formation relative to another part. Examples of parameters that may be monitored include a relative distribution of water production along a lateral or between laterals in multiple interconnected well systems, a formation fluid composition, or a measure of rock heterogeneity. Preferably, the parameter relates to a well or formation. It will be appreciated that when a parameter is said to relate to a well or formation, that well refers to the constructed apparatus for extracting the hydrocarbon, while formation refers to the natural structure in which the hydrocarbon is located and from which it is extracted via the well.

According to a second aspect of the invention there is provided a method of monitoring a parameter of a hydrocarbon well, pipeline or formation, the method comprising:
introducing a tracer into the hydrocarbon well, pipeline or formation;
producing a fluid from the hydrocarbon well, pipeline or formation; and
analysing the fluid to determine if the tracer is present in the fluid;
characterised in that the tracer comprises a halogenated alkoxylated-benzoic acid, an alkoxylated benzene sulfonic acid, a salt of a halogenated alkoxylated-benzoic acid or a salt of an alkoxylated benzene sulfonic acid. Preferably the tracer comprises a salt of a halogenated alkoxylated-benzoic acid or a salt of an alkoxylated benzene sulfonic acid.

In a preferred aspect of the invention the tracer comprises a compound, or a salt thereof, of formula 1:

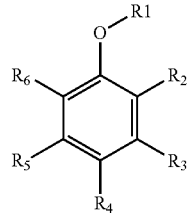

Formula 1 wherein $R_1$ is selected from the group consisting of $C_nF_xCl_yH_{(2n+1-x-y)}$ where n=1, 2 or 3, and x and y are integers such that $0 \leq x+y \leq 2n+1$, wherein at least one of $R_2$, $R_3$, $R_4$, $R_5$ and $R_6$ is carboxylic acid (COOH) or sulfonic acid ($SO_3H$), wherein the remainder of $R_2$, $R_3$, $R_4$, $R_5$ and $R_6$ are selected from the group consisting of F, Cl, Br, H, $B(OH)_2$, $C_mF_jCl_kBr_lH_{(2m+1-j-k-l)}$, where m=1, 2 or 3, each of j, k and l are integers such that $0 \leq j+k+l \leq 2m+1$, and $O-C_pF_rCl_sBr_t H_{(2p+-r-s-t)}$, where p=1, 2 or 3, and r, s and t are integers such that $0 \leq r+s+t \leq 2p+1$, and wherein either at least one of $R_2$, $R_3$, $R_4$, $R_5$ and $R_6$ is sulfonic acid, or at least one of $R_1$, $R_2$, $R_3$, $R_4$, $R_5$ and $R_6$ is halogenated, or both.

Thus an aspect of the invention provides a method of monitoring a parameter of a hydrocarbon well, pipeline or formation, the method comprising:
introducing a tracer into the hydrocarbon well, pipeline or formation;
producing a fluid from the hydrocarbon well, pipeline or formation; and
analysing the fluid to determine if the tracer is present in the fluid;
characterised in that the tracer comprises a compound, or a salt thereof, of formula 1:

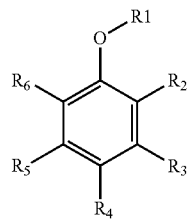

Formula 1 wherein $R_1$ is selected from the group consisting of $C_nF_xCl_yH_{(2n+1-x-y)}$ where n=1, 2 or 3, and x and y are integers such that $0 \leq x+y \leq 2n+1$, wherein at least one of $R_2$, $R_3$, $R_4$, $R_5$ and $R_6$ is carboxylic acid (COOH) or sulfonic acid ($SO_3H$), wherein the remainder of $R_2$, $R_3$, $R_4$, $R_5$ and $R_6$ are selected from the group consisting of F, Cl, Br, H, $B(OH)_2$, $C_mF_jCl_kBr_lH_{(2m+1-j-k-l)}$, where m=1, 2 or 3, each of j, k and l are integers such that $0 \leq j+k+l \leq 2m+1$, and $O-C_pF_rCl_sBr_tH_{(2p+1-r-s-t)}$, where p=1, 2 or 3, and r, s and t are integers such that $0 \leq r+s+t \leq 2p+1$, and wherein either at least one of $R_2$, $R_3$, $R_4$, $R_5$ and $R_6$ is sulfonic acid, or at least one of $R_1$, $R_2$, $R_3$, $R_4$, $R_5$ and $R_6$ is halogenated, or both.

Further aspects of the tracer may be as set out above for the tracer of the first aspect of the invention.

The method may monitor a parameter of a hydrocarbon well or formation. The tracer may be introduced into the well by any method. For example, the introducing may comprise injecting the tracer into the well or formation. For example, the tracer may be injected into the well or formation of which the parameter is being monitored. The tracer may be injected into an adjacent well or formation and thus be introduced into the formation via the adjacent well or formation. The tracer may be introduced into the well or formation during construction of the well. For example, the tracer may be provided comprised in a solid article incorporated into or attached to a component part of the well, such as a filter, mesh, sand screen, in-flow control device or valve. The tracer may be introduced into the well or formation as a liquid, for example in solution or as an emulsion with injection fluid, such as drilling fluids, hydraulic fracturing fluids or injection water. The tracer may be introduced into the well as a solid, for example as slurry with drilling fluids, hydraulic fracturing fluids or injection water, or as a solid or liquid encapsulated in another solid. The tracer may be introduced into the well or formation by introducing a proppant which comprises the tracer.

The fluid produced may comprise water, for example the fluid may comprise a mixture of hydrocarbon and water. The analysing may be performed on-line, at-line or off-line. In the latter cases, samples of the fluid may be taken and transferred to a laboratory, either at the drilling location (at-line) or at a remote location (off-line) for analysis. Preferably the analysing is carried out using GC-MS. An advantage of the method of the invention may be that the tracer comprising a compound (or a salt thereof) of formula 1 may be readily distinguishable from prior art tracers, many of which now already contaminate a large number of wells and formation, using GC-MS.

The analysis may be qualitative, in that it determines whether the tracer is present or not, or it may be quantitative in that it determines if the tracer is present by determining the level, for example the concentration, of the tracer in the fluid. Preferably the analysis determines the level at which the tracer is present in the fluid. The level may be determined as a ratio of parts of tracer per part of fluid for example. Thus the method may comprise determining the concentration of the tracer in the fluid.

The tracer may comprise a halogenated alkoxylated-benzoic acid. The tracer may comprise an alkoxylated benzene sulfonic acid, which may be a halogenated benzene sulfonic acid. The tracer may comprise a salt of a halogenated alkoxylated-benzoic acid. The tracer may comprise a halogenated alkoxylated-benzoate. The tracer may comprise a salt of an alkoxylated benzene sulfonic acid, which may be a salt of a halogenated alkoxylated benzene sulfonic acid.

The tracer may comprise an alkoxylated benzene sulfonate, which may be a halogenated alkoxylated benzene sulfonate. Preferably the salt is a sodium salt. Preferably the tracer comprises a salt, preferably a sodium salt, of a compound of formula 1. The tracer may consist of the acid or a salt thereof. The acid itself, or a salt thereof, may be the tracer.

It will be appreciated that the acid or the salt may dissociate to form an anion when dissolved in water. The anion may therefore act as the tracer when the acid or salt is dissolved. When the tracer is said to comprise the acid or salt it will be understood as encompassing the situation in which the anion of the dissolved acid or salt may act as the tracer. The analysis of the fluid for the tracer may analyse for the tracer in its dissolved state, or may involve steps of extracting the tracer and subsequently analysing the extracted tracer. It will be appreciated that the analysis method may include steps that convert, for example, a tracer salt to the corresponding acid or anion, or to both, as part of the analysis method. For example, when a halogenated alkoxylated-benzoate salt is used as the tracer, the salt may be present in a dissociated form in the fluid produced from the well and the analysing of the fluid to determine if the tracer is present in the fluid may involve a GC-MS analysis of the fluid that includes steps of converting the salt into the corresponding carboxylic acid and a final mass spectrometry step that detects the corresponding anion in the mass spectrometer. Nevertheless, the halogenated alkoxylated-benzoate salt will be understood as being the tracer and being detected by the analysis method.

The tracer may be a salt of a compound selected from the group consisting of 3,5-difluoro-4-methoxybenzoic acid; 2,4-difluoro-3-methoxybenzoic acid; and 3-(Difluoromethoxy)benzoic acid.

Examples of tracers according to the invention include: fluoro-methoxybenzoic acids, difluoro-methoxybenzoic acids, chloro-methoxybenzoic acids, dichloro-methoxybenzoic acids, fluoro-chloro-methoxybenzoic acids, (fluoromethoxy)-benzoic acids, (difluoromethoxy)-benzoic acids and (trifluoromethoxy)-benzoic acids.

For example, fluoro-methoxybenzoic acids include: 3-fluoro-2-methoxybenzoic acid, 4-fluoro-2-methoxybenzoic acid, 5-fluoro-2-methoxybenzoic acid, 6-fluoro-2-methoxybenzoic acid, 2-fluoro-3-methoxybenzoic acid, 4-fluoro-3-methoxybenzoic acid, 5-fluoro-3-methoxybenzoic acid, 6-fluoro-3-methoxybenzoic acid, 2-fluoro-4-methoxybenzoic acid and 3-fluoro-4-methoxybenzoic acid.

For example, difluoro-methoxybenzoic acids include: 3,4-difluoro-2-methoxybenzoic acid, 3,5-difluoro-2-methoxybenzoic acid, 3,6-difluoro-2-methoxybenzoic acid, 4,5-difluoro-2-methoxybenzoic acid, 4,6-difluoro-2-methoxybenzoic acid, 5,6-difluoro-2-methoxybenzoic acid, 2,4-difluoro-3-methoxybenzoic acid, 2,5-difluoro-3-methoxybenzoic acid, 2,6-difluoro-3-methoxybenzoic acid, 4,5-difluoro-3-methoxybenzoic acid, 4,6-difluoro-3-methoxybenzoic acid, 5,6-difluoro-3-methoxybenzoic acid, 2,3-difluoro-4-methoxybenzoic acid, 2,5-difluoro-4-methoxybenzoic acid, 2,6-difluoro-4-methoxybenzoic acid and 3,5-difluoro-4-methoxybenzoic acid.

Examples of tracers according to the invention include: fluoro-ethoxybenzoic acids, difluoro-ethoxybenzoic acids, chloro-ethoxybenzoic acids, dichloro-ethoxybenzoic acids, fluoro-chloro-ethoxybenzoic acids and (fluoroethoxy)-benzoic acids.

Examples of tracers according to the invention include: fluoro-methoxybenzene sulfonic acids, difluoro-methoxybenzene sulfonic acids, chloro-methoxybenzene sulfonic acids, dichloro-methoxybenzene sulfonic acids, fluorochloro-methoxybenzene sulfonic acids, (fluoromethoxy)-benzene sulfonic acids, (difluoromethoxy)-benzene sulfonic acids and (trifluoromethoxy)-benzene sulfonic acids.

Examples of tracers according to the invention include: methyl-methoxybenzene sulfonic acids, dimethyl-methoxybenzene sulfonic acids, methyl-ethoxybenzene sulfonic acids, dimethyl-ethoxybenzene sulfonic acids and ethyl-methoxybenzene sulfonic acids.

Examples of such acids include: 3-methyl-2-methoxybenzene sulfonic acid, 3,4-dimethyl-2-methoxybenzene sulfonic acid, 3,5-dimethyl-2-methoxybenzene sulfonic acid, 4,6-dimethyl-2,3-dimethoxybenzene sulfonic acid and 3-methyl-4-ethyl-2-methoxybenzene sulfonic acid.

Examples of tracers according to the invention include salts, preferably sodium salts, of the acids above.

Examples of tracer salts include: 3-methyl-2-methoxybenzene sulfonate, 4-methyl-2-methoxybenzene sulfonate, 5-methyl-2-methoxybenzene sulfonate, 6-methyl-2-methoxybenzene sulfonate, 2-methyl-3-methoxybenzene sulfonate, 4-methyl-3-methoxybenzene sulfonate, 5-methyl-3-methoxybenzene sulfonate, 6-methyl-3-methoxybenzene sulfonate, 2-methyl-4-methoxybenzene sulfonate and 3-methyl-4-methoxybenzene sulfonate.

Examples of tracer salts include: 2-(fluoromethoxy)benzoate, 3-(fluoromethoxy)benzoate, 4-(fluoromethoxy)benzoate, 2,3-di(fluoromethoxy)benzoate, 2,4-di(fluoromethoxy)benzoate, 2,5-di(fluoromethoxy)benzoate, 2,6-di(fluoromethoxy)benzoate, 3,4-di(fluoromethoxy)benzoate, 3,5-di(fluoromethoxy)benzoate, 2-(difluoromethoxy)benzoate, 3-(difluoromethoxy)benzoate and 4-(difluoromethoxy)benzoate, Examples of tracer salts include: 3,4-difluoro-2-methoxybenzoate, 3,5-difluoro-2-methoxybenzoate, 3,6-difluoro-2-methoxybenzoate, 4,5-difluoro-2-methoxybenzoate, 4,6-difluoro-2-methoxybenzoate, 5,6-difluoro-2-methoxybenzoate, 2,4-difluoro-3-methoxybenzoate, 2,5-difluoro-3-methoxybenzoate, 2,6-difluoro-3-methoxybenzoate, 4,5-difluoro-3-methoxybenzoate, 4,6-difluoro-3-methoxybenzoate, 5,6-difluoro-3-methoxybenzoate, 2,3-difluoro-4-methoxybenzoate, 2,5-difluoro-4-methoxybenzoate, 2,6-difluoro-4-methoxybenzoate and 3,5-difluoro-4-methoxybenzoate.

Examples of tracer salts include: 3-chloro-2-methoxybenzene sulfonate, 4-chloro-2-methoxybenzene sulfonate, 5-chloro-2-methoxybenzene sulfonate, 6-chloro-2-methoxybenzene sulfonate, 2-chloro-3-methoxybenzene sulfonate, 4-chloro-3-methoxybenzene sulfonate, 5-chloro-3-methoxybenzene sulfonate, 6-chloro-3-methoxybenzene sulfonate, 2-chloro-4-methoxybenzene sulfonate and 3-chloro-4-methoxybenzene sulfonate.

It will be appreciated that features described in relation to one aspect of the invention may be equally applicable in another aspect of the invention. For example, features described in relation to the use of the tracer of the invention, may be equally applicable to the method of the invention, and vice versa. Some features may not be applicable to, and may be excluded from, particular aspects of the invention.

DESCRIPTION OF THE DRAWINGS

Embodiments of the present invention will now be described, by way of example, and not in any limitative sense, with reference to the accompanying drawings, of which:

FIG. 1 is a GC-MS plot comparing a tracer for use in an embodiment of the invention to prior art tracers.

EXAMPLES

Example tracers Ex 1 to Ex 3 were analysed to determine their detectability using GC-MS. The detectability was determined by diluting the tracer using acetonitrile to levels of 10 ppm and analysing it on a GC-MS to determine the retention time. The tracers were then further diluted to 25, 30, 35 and 40 ppb using deionised water. The tracers were then extracted using solid phase extraction and analysed by GC-MS. Prior to extraction the solution is acidified to convert all of the tracer to the acid form. In this way either the anion (for example, the dissolved salt) or the acid can prepared for analysis. For the solid phase extraction 25 ml of the tracer solution with 0.5 ml of internal standard of 2,6-bis(trifluoroethyl)-benzoic acid at a concentration of 1.05 ppm and 0.25 ml of concentrated HCl were run on a solid phase extraction instrument. This technique concentrates the solution 20-fold, e.g. to 40 to 800 ppb. After this technique, 1 ml of sample was added to a GC vial, as well as 0.5 ml of 4% derivatising agent 2,3,4,5,6-pentafluorobenzyl bromide made up with acetone. The sample was heated at 95° C. for 30 minutes and then run on the GC-MS with the following parameters:

GC—Oven

| Column | Rxi-5 ms |
|---|---|
| Equilibrium Time | 0.5 min |
| Max Temperature | 325° C. |
| Oven Program | 70° C. for 3 min then 10° C./min to 280° C. for 6 min |
| Oven Run Time | 30 min |

GC—Front SS Inlet He

| Mode | Split |
|---|---|
| Heater | 280° C. |
| Pressure | 10.57 psi |
| Total Flow | 121.71 ml/min |
| Septum Purge Flow | 5 ml/min |
| Split Ratio | 100:1 |
| Split Flow | 115.55 ml/min |

MS—NCI

| Acquisition Mode | SIM |
|---|---|
| Solvent Delay | 4.00 |

Since the purpose of the study was to compare performance between the tracers, the LoD was calculated in arbitrary units that permit direct comparison between the examples. The LoD was calculated based on the standard error of the results obtained, which is used to determine the level at which the tracer could be reliably detected. The results are shown in table 1 along with data for prior art comparative tracers PA 1 to PA 2. Note that lower numbers indicate a lower, and hence more desirable, limit of detection.

Example PA 1 is a salt of 2-Fluorobenzoic Acid. Example PA 2 is a salt of 2,6-Difluorobenzoic Acid. Both PA1 and PA2 are known as water tracers.

Examples Ex 1 to Ex 3 are tracers according to the present invention. Ex 1 is a salt of 3-(Difluoromethoxy)benzoic acid, Ex 2 is a salt of 3,5-Difluoro-4-methoxybenzoic acid and Ex 3 is a salt of 2,4-Difluoro-3-methoxybenzoic acid.

| Tracer | LoD |
|--------|--------|
| PA 1 | 0.0577 |
| PA 2 | 0.2948 |
| Ex 1 | 0.0825 |
| Ex 2 | 0.0787 |
| Ex 3 | 0.1000 |

It can be seen that the tracers of the invention are at least as suitable if not more so than the prior art tracers. A simple test involving allowing a known quantity of tracer to equilibrate between a water phase and a hydrocarbon phase and then determining what percentage of the tracer was in the water phase also indicated that the tracers of the invention show adequate preference for the water phase when compared to the prior art tracers.

Theoretical calculations show that the log P (the value corresponding to the base-10 logarithm of the ratio of the concentrations of the substance in octanol and water) value is negative. This demonstrates a preference for the water phase over the oil phase for these tracers.

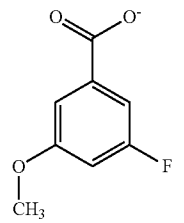

log P (predicted) = -1.91

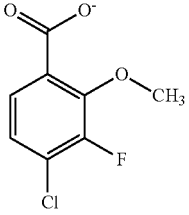

log P (predicted) = -1.31

Turning to FIG. 1, a GC-MS plot shows the detection of the three tracers according to the invention 1, 2 and 3 in a sample that also contains two prior art sodium monofluorobenzoate tracers 4 and 5 and two prior art sodium difluorobenzoate tracers 6 and 7. The two monofluorobenzoate tracers 4 and 5 both exhibit an ion of m/z=139, and are acquired between 18 and 18.5 minutes. The difluorobenzoate tracers 6 and 7 both exhibit an ion of m/z=157, one 6 acquired at around 17.5 minutes and one 7 acquired at around 18.5 minutes. By contrast, the tracers of the present invention 1, 2 and 3 are clearly distinguished from the prior art tracers. Most advantageously, the distinction is in terms of both the ion (m/z=187) and the time of acquisition (between 19.25 minutes and 20.25 minutes). In a potentially crowded analysis of multiple tracers (some applications requiring 40 tracers or more), such a clear distinction in terms of both time and mass may be a significant advantage of the tracers of the invention.

It will be appreciated by persons skilled in the art that the above embodiments have been described by way of example only, and not in any limitative sense, and that various alterations and modifications are possible without departure from the scope of the invention as defined by the appended claims.

The invention claimed is:

1. A method of monitoring a parameter of a hydrocarbon well, pipeline or formation, the method comprising:
   introducing a tracer into the hydrocarbon well, pipeline or formation;
   producing a fluid from the hydrocarbon well, pipeline or formation; and
   analysing the fluid to determine if the tracer is present in the fluid;
   wherein the tracer comprises a halogenated alkoxylated-benzoic acid, an alkoxylated benzene sulfonic acid, a salt of a halogenated alkoxylated-benzoic acid, or a salt of an alkoxylated benzene sulfonic acid.

2. The method according to claim 1, wherein the tracer comprises a salt of a halogenated alkoxylated-benzoic acid or a salt of an alkoxylated benzene sulfonic acid.

3. The method according to claim 1, wherein the tracer comprises a compound, or a salt thereof, of formula 1:

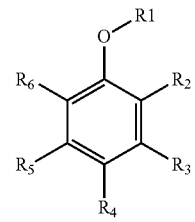

Formula 1 wherein $R_1$ is $C_nF_xCl_yH_{(2n+1-x-y)}$ where n=1, 2 or 3, and x and y are integers such that $0 \leq x+y \leq 2n+1$, wherein at least one of $R_2$, $R_3$, $R_4$, $R_5$ and $R_6$ is carboxylic acid or sulfonic acid, wherein the remainder of $R_2$, $R_3$, $R_4$, $R_5$ and $R_6$ are selected from the group consisting of F, Cl, Br, H, $B(OH)_2$, $C_mF_jCl_kBr_lH_{(2m+1-j-k-l)}$, where m=1, 2 or 3, each of j, k and l are integers such that $0 \leq j+k+l \leq 2m+1$, and $O-C_pF_rCl_sBr_tH_{(2p+1-r-s-t)}$, where p=1, 2 or 3, and r, s and t are integers such that $0 \leq r+s+t \leq 2p+1$, and wherein either at least one of $R_2$, $R_3$, $R_4$, $R_5$ and $R_6$ is sulfonic acid, or at least one of $R_1$, $R_2$, $R_3$, $R_4$, $R_5$ and $R_6$ is halogenated, or both.

4. The method according to claim 3, wherein $R_1$ is $C_nX_yH_{(2n+1-y)}$ where n=1, 2 or 3, $0 \leq y \leq 2n+1$ and X is one of F or Cl.

5. The method according to claim 4, wherein $R_1$ is $C_nX_yH_{(2n+1-y)}$ where n=1, 2 or 3, $1 \leq y \leq 2n+1$ and X is one of F or Cl.

6. The method according to claim 4, wherein $R_1$ is selected from the group consisting of $CH_3$, $C_2H_5$, $C_3H_7$, $CFH_2$, $CF_2H$, $CF_3$, $CClH_2$, $CCl_2H$ and $CCl_3$.

7. The method according to claim 6, wherein $R_1$ is selected from the group consisting of $CH_3$, $CFH_2$, $CF_2H$, and $CF_3$.

8. The method according to claim 3, wherein the remainder of $R_2$, $R_3$, $R_4$, $R_5$ and $R_6$ are selected from the group consisting of F, Cl, Br, H, $C_mX_jH_{(2m+1-j)}$ where m=1, 2 or 3, $0 \leq j \leq 2m+1$ and X is one of F, Cl or Br, and $O-C_pX_rH_{(2p+1-r)}$, where p=1, 2 or 3, $0 \leq r \leq 2p+1$ and X is one of F, Cl or Br.

9. The method according to claim 8, wherein the remainder of $R_2$, $R_3$, $R_4$, $R_5$ and $R_6$ are selected from the group consisting of F, Cl, Br, H, $CH_3$, $C_2H_5$, $C_3H_7$, $CFH_2$, $CF_2H$, $CF_3$, O—$CH_3$, O—$C_2H_5$, O—$C_3H_7$, O—$CFH_2$, O—$CF_2H$, O—$CF_3$, O—$CClH_2$, O—$CCl_2H$ and O—$CCl_3$.

10. The method according to claim 9, wherein the remainder of $R_2$, $R_3$, $R_4$, $R_5$ and $R_6$ are selected from the group consisting of F, Cl, Br, H, $CH_3$, $C_2H_5$, $C_3H_7$, $CFH_2$, $CF_2H$, and $CF_3$.

11. The method according to claim 3, wherein at least one of $R_1$, $R_2$, $R_3$, $R_4$, $R_5$ and $R_6$ is halogenated.

12. The method according to claim 11, wherein at least one of $R_1$, $R_2$, $R_3$, $R_4$, $R_5$ and $R_6$ is fluorinated, chlorinated or brominated.

13. The method according to claim 12, wherein at least one of $R_1$, $R_2$, $R_3$, $R_4$, $R_5$ and $R_6$ is fluorinated or chlorinated.

14. The method according to claim 13, wherein at least one of $R_1$, $R_2$, $R_3$, $R_4$, $R_5$ and $R_6$ is fluorinated.

15. The method according to claim 3, wherein the tracer is an alkoxylated benzene sulfonic acid.

16. The method according to claim 15, wherein $R_1$ is $C_nH_{(2n+1)}$ where n=1, 2 or 3.

17. The method according to claim 16, wherein $R_1$ is $CH_3$.

18. The method according to claim 15, wherein the remainder of $R_2$, $R_3$, $R_4$, $R_5$ and $R_6$ are selected from the group consisting of H, $C_mH_{(2m+1)}$ where m=1, 2 or 3, and O—$C_pH_{(2p+1)}$, where p=1, 2 or 3.

19. The method according to claim 18, wherein the remainder of $R_2$, $R_3$, $R_4$, $R_5$ and $R_6$ are selected from the group consisting of H, $CH_3$, $C_2H_5$ and $C_3H_7$.

20. The method according to claim 3, wherein none of $R_2$, $R_3$, $R_4$, $R_5$ and $R_6$ is carboxylic acid.

21. The method according to claim 3, wherein none of $R_2$, $R_3$, $R_4$, $R_5$ and $R_6$ is sulfonic acid.

22. The method according to claim 21, wherein at least one of $R_1$, $R_2$, $R_3$, $R_4$, $R_5$ and $R_6$ is fluorinated or chlorinated.

23. The method according to claim 22, wherein at least one of $R_1$, $R_2$, $R_3$, $R_4$, $R_5$ and $R_6$ is fluorinated.

24. The method according to claim 1, wherein the tracer is a sodium salt.

* * * * *